United States Patent [19]

Axelsson

[11] 4,411,623

[45] Oct. 25, 1983

[54] DEVICE FOR APPLYING TOOTHPASTE

[76] Inventor: Per A. T. Axelsson, Drottninggatan 27, S-652 25 Karlstad, Sweden

[21] Appl. No.: 313,489

[22] Filed: Oct. 21, 1981

[30] Foreign Application Priority Data

Oct. 31, 1980 [SE] Sweden .............................. 8007683

[51] Int. Cl.³ ............................................. A61G 17/02
[52] U.S. Cl. ...................................... 433/80; 222/107
[58] Field of Search .................... 433/80, 89; 222/107, 222/92, 572

[56] References Cited

U.S. PATENT DOCUMENTS

| | | | |
|---|---|---|---|
| 838,648 | 12/1906 | Robertson | 433/80 |
| 1,331,271 | 2/1920 | MacGregor . | |
| 1,341,736 | 1/1920 | Cruttenden | 433/89 |
| 1,696,486 | 12/1928 | Jefferies | 433/89 |
| 1,958,332 | 5/1934 | Carpenter | 433/80 |
| 2,222,267 | 11/1940 | Schnabel | 222/107 |
| 3,442,022 | 1/1971 | Axelsson . | |
| 3,878,977 | 4/1975 | Carlisle | 222/107 |
| 3,939,871 | 2/1976 | Dickson . | |

FOREIGN PATENT DOCUMENTS

| | | | |
|---|---|---|---|
| 76332 | 8/1928 | Sweden . | |
| 167116 | 7/1952 | Sweden . | |
| 368334 | 7/1974 | Sweden . | |
| 902736 | 8/1962 | United Kingdom | 222/107 |

*Primary Examiner*—Robert Peshock
*Attorney, Agent, or Firm*—Cushman, Darby & Cushman

[57] ABSTRACT

An applicator device for the application of paste directly upon the teeth, particularly in the interspaces between teeth intended to be used by the dental profession or when cleaning the teeth at home. The object of the invention is to create an applicator device of a simple design economically so that it need not be refilled but may be discarded after use. The device should also be easy to handle and shaped such that its tip can reach each and every interspace. The device comprises an integrally formed plastics material tube having a comparatively wide, compressible handle portion defining an internal paste container, an adjoining comparatively narrow and quite long conduit portion, and a laterally directed tapering nozzle portion at the end of the conduit portion through which portion the paste may be discharged into the interspaces between teeth.

4 Claims, 9 Drawing Figures

U.S. Patent      Oct. 25, 1983      4,411,623

DEVICE FOR APPLYING TOOTHPASTE

BACKGROUND OF THE INVENTION

The present invention relates to a non-refillable applicator device for direct application of paste upon and particularly between teeth in connection with cleaning, polishing or similar surface treatment thereof performed either professionally by dentists or dental hygienists, or by the patient himself.

Normal teeth cleaning by means of toothbrushes with tooth paste applied thereto is not completely satisfactory because the proximate faces of the teeth, i.e. the faces bordering the interspaces between the teeth, are difficult to reach. Extensive research has revealed that the frequency of tooth diseases is considerably reduced when personal teeth care is completed with recurrent cleaning by dental personnel—the lateral tooth faces being polished with abrasive pastes and with the use of tooth picks or similar devices introduced into the interspaces between teeth and reciprocated either manually or mechanically, e.g. by such tools as are described in the British Pats. Nos. 1,211,150 and 1,296,543.

Hitherto, it has not been possible to apply paste into the interspaces between teeth in a completely satisfactory manner. With professional teeth cleaning, the abrasive paste is normally stored in tubes or jars with screw caps. At each occasion of treatment a sufficient quantity is obtained from said tubes or jars and placed in a small cup of a discardable type, from there the paste is subsequently transferred to the teeth by various instruments. This is a complicated method which is unhygienic in view of the risk of infection and can also cause the paste to become dry and lose its abrasive properties. The result with such procedure is—as when applying the paste with a tooth brush at home—that most of the paste is applied on those faces of the teeth which are most easily reached and that require the least cleaning, whereas the teeth interspaces are less favoured.

In connection with clinical teeth treatment it is known to use syringes of various kinds and for different purposes, such as for antiseptic rinsing and for the introduction of medicaments or, for example, impression masses in the mouth of the patient.

SUMMARY OF THE INVENTION

The object of the invention is to provide an applicator device for applying paste to teeth which is considerably simpler and cheaper than existing syringes for other purposes and which is well suited to the above-mentioned tooth cleaning purpose. The basic concept of the invention is that the applicator device should only be used for one and the same patient and should be so small and simple that it may very well be discarded after use—thereby saving the work of sterilization and refilling of a paste container.

The non-refillable applicator device of the invention for the application of paste directly upon and particularly between the teeth for the subsequent cleaning, polishing or like treatment, comprises a single-layer tubular body of a plastics material which as a single integral member part of which forms a handle portion suitable for being grasped by two or more fingers of the hand and constituting a container for paste and a conduit portion adjoining the handle portion and extending substantially in the length direction of the handle portion, extends in straight or slightly curved direction and is of tapering cross-section considerably less than that of the handle portion and of a length approximately corresponding to the distance between the incisors and the back molars; said conduit portion merging via a bend into a pointed nozzle portion forming an outlet for the paste and directed at preferably right angles to the length direction of the conduit portion, the wall of the conduit and nozzle portions of the tubular plastics material body being comparatively thick in order to provide stiffness thereof, and the wall of the handle portion being comparatively thinner in order to permit its flattening compression to expel the paste.

BRIEF DESCRIPTION OF THE DRAWINGS

The invention will be described further, by way of example, with reference to the accompanying drawing, in which.

DESCRIPTION OF THE PREFERRED EMBODIMENT

Figure 1:
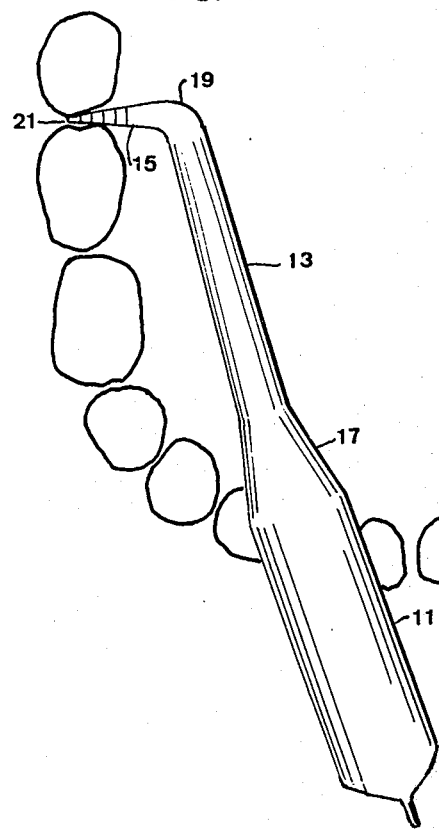
FIG. 1 is a plan view of a preferred embodiment of a syringe or applicator device illustrating its position of use in the mouth of a patient.
Figure 2:
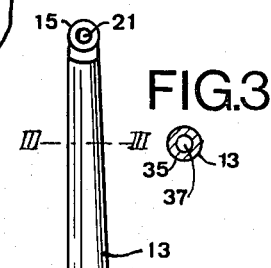
FIG. 2 is an elevation of the device of FIG. 1 viewed from the left-hand side and at right angles to the view of FIG. 1.
Figure 3:
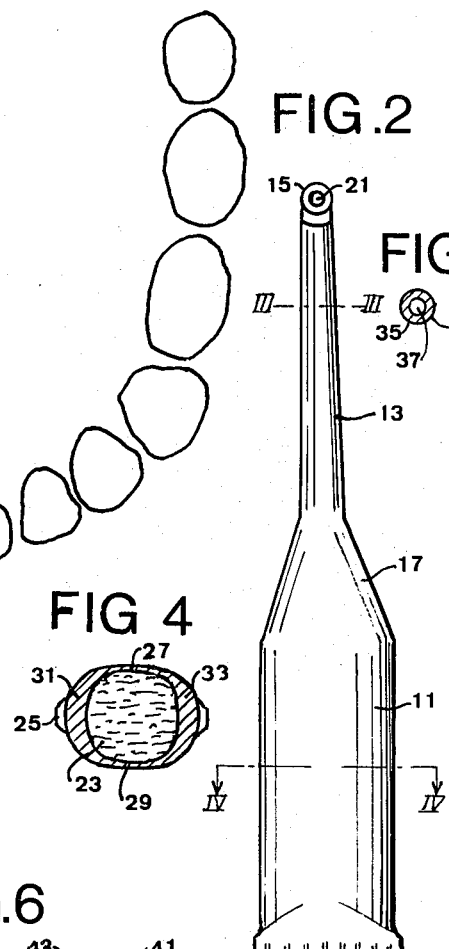
FIGS. 3 and 4 are cross-sectional views taken along the lines III—III and IV—IV of FIG. 2, respectively.
Figure 4:
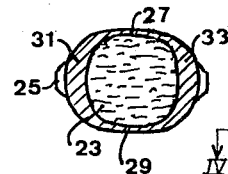

A syringe or applicator device is shown in FIGS. 1 to 4 comprising a unitary moulded body of a suitable plastics material, such as polyvinyl chloride or polyethylene, which forms a tube having a straight portion and a bent portion of varying cross-sections and having a wall of unitary single layer of varying thickness. The tubular body forms in consecutive order, a handle portion 11, a conduit portion 13 and a nozzle portion 15. The handle portion 11 which is the widest and of substantially uniform wall thickness over its entire length, is connected, via a converging conical transition portion 17, to the conduit portion 13, the cross-sectional area of which portion 13 is considerably less than that of handle portion, e.g. a third to a tenth thereof. At its other end the conduit portion 13 merges via a bend 19 into the nozzle portion 15 which is conically tapered and has an outlet aperture 21 at its tip. The conduit portion 13 is straight and of uniform diameter or slightly conical or convergers. The nozzle portion 15 is directed sidewise (approximately at right angles to portion 13). The conduit portion 13 may be bent near or distant from the bend 19 at an angle opposite to that of said bend. Such a counter-angle is usual in many dental instruments in order to improve the accessibility to the concave inner side of the teeth row. As an alternative, the entire conduit portion 13 may be slightly curved.

The handle portion 11 forms a container 23 for paste and is permanently closed after filling by compressing its rear end into a straight joint 25 which is heat-sealed. The paste filling is intended to be squeezed out and therefore the container is made soft and resilient so that it can be compressed by finger force. When the container is filled, the cross-section of the portion 11 is oval and it will be accordingly flatter as the paste is discharged. The container wall is thin along the broad sides 27, 29 and thicker along the narrow sides 31, 33—the handle portion being easily deformable when squeezing out the paste and also retaining its resistance to bending and twisting forces even after discharge of most of the paste so that the manipulation thereof is not impaired. The conduit and nozzle portions 13, 15 of a considerably lesser cross-sectional area have the required stiffness due to the wall 35 (FIG. 3) being rigid and several times thicker than that of the wall portions 27, 29. The passage 37 in these regions tapers gradually from the container 11 to the outlet aperture 21, and the transition portion 17 connects the interior of the container 11 with conduit portion 13 with the least possible resistance to the flow of the paste.

The length of the handle portion 11 is preferably 3 to 4 centimeters which is sufficient to permit such to be conveniently grasped between the thumb and the forefinger of the hand with the possible aid of one or more fingers. This corresponds to a maximum filling with paste of 20 to 40 milliliters. The length of the conduit portion is about 4 to 6 centimeters, which approximately corresponds to the distance between the incisors and the back molars and is sufficient for placing the device in all required positions while being held by fingers outside the mouth. This is apparent from FIG. 1 which shows the position of the device when applying paste from the tongue side into the interspace between the two rearmost molars, a spot where the cleaning is troublesome and therefore most important to treat in order to prevent parodontitis.

Figure 5:
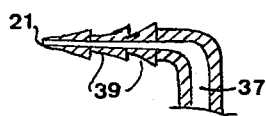
FIG. 5 is an enlarged fragmentary detail of the nozzle part of the device.

The nozzle portion 15 is mainly conical and of a preferred length of about 15 millimeters. As shown in FIG. 5, a passage 37 therein gradually tapers towards the orifice 21 and a number of annular grooves 39 formed on the outside of the nozzle part weakens the material and makes it easy to break or cut off the tip in order to shorten the same when the orifice has been clogged or when it is desired to increase the size of the orifice. Outlet orifices of a diameter of 1 to 3 millimeters are useful for teeth interspaces of all common sizes.

Figure 6:
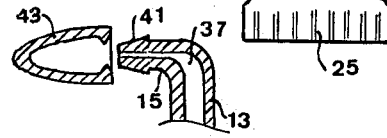
FIG. 6 illustrates a modified design of the nozzle part of the device with closure cap.

As an alternative, the nozzle part may be designed, as shown in FIG. 6, with an annular end flange 41 upon which a loose cap 43 can be snapped when it is desired to close the orifice and prevent the paste therein from drying.

Figure 7:
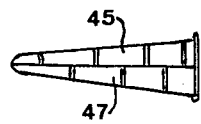
FIGS. 7, 8 and 9 illustrate a cap nozzle from three different directions.
Figure 8:
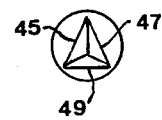
Figure 9:
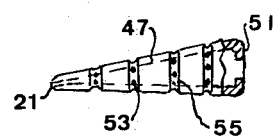

In the embodiment of FIGS. 7 to 9, an attachable cap nozzle is shown on its own for snap-fit onto the end of conduit portion 13 and comprises a hollow body of plastics material having a triangular cross-section tapering towards the tip. The lateral faces 45, 47 forming an angle of about 30 to 40 degrees to each other, are meant to contact the teeth on opposite sides of the interspace into which the tip of the device is inserted, whereas the third, narrower and smooth side 49 is meant to press down and slide against the gum papilla. The cap nozzle is attached so as to be rotatable, its inwardly directed end flange 51 overlapping the annular flange 41 (FIG. 6). Therefore, when inserted into an interspace between teeth the cap nozzle turns automatically into the proper position for contacting the teeth sides. The snap fit normally retains the cap nozzle upon the rest of the device but allows it removal for replacement by a new one, e.g. of another shape or size. From the inner cavity of the cap nozzle communicating with the passage 37 (FIG. 6) paste is discharged through outlet orifices located at the extreme tip 21 and/or at the lateral faces 45, 47. As shown in FIG. 9, outlet orifices 53 are preferably placed at the bottom of transverse grooves 55 in the lateral faces—the paste being securely applied direct upon the approximate teeth faces. The shape of the device and the free rotatability of its tip assures the accessibility to the interspaces between all teeth in the upper and lower teeth rows both from the tongue side as well as the cheek side.

The above-described device is primarily intended for the application of abrasive or polishing pastes in clinical treatment by dentists or dental hygienists although identical or slightly modified designs can also serve for home use in the application of dentifrice preceding brushing with ordinary tooth brushes or cleaning with tooth picks.

The above-described embodiment is merely an example of one realization of the invention. It is obvious that modifications in respect of dimensions and other details are possible without departing from the scope of the invention as set forth in the following claims.

I claim:

1. A non-refillable applicator device for the application of toothpaste directly upon teeth for cleaning, polishing, or similar surface treatment thereof, comprising: an integrally formed tubular body of plastics material having a handle portion shaped and dimensioned so as to be capable of being grasped by two or more fingers of the hand and also defining interior space means and constituting a container of paste, said handle portion having a non-circular cross-section over the greater part of its length and the wall of said handle portion being thinner along the broad sides than along the narrower sides thereof; a conduit portion extending from said handle portion substantially in the direction of the length of the handle portion and being of tapering cross-section considerably less than the cross-section of said handle portion and of a length approximately corresponding to the distance between the incisors and the back molars of a human; a pointed nozzle portion forming outlet means for paste; a bent portion interconnecting said pointed nozzle portion and said conduit portion so that said nozzle portion is directed at an angle to the direction of extension of said conduit portion; the walls defining the conduit and nozzle portions of the tubular plastics body being comparatively thick in order to provide stiffness thereof, and the wall of the handle portion being comparatively thin in order to enable such to be compressed to permit paste to be expelled; and said nozzle portion having a triangular cross-section gradually decreasing in cross-section from said bent portion to an end thereof for outlet of paste.

2. A device according to claim 1, wherein the nozzle part is shaped with one or more weakening annular grooves whereby its tip is made easier to be removed.

3. A device according to claim 1 wherein said nozzle portion includes a cap nozzle rotatably attached thereto, said cap nozzle being suitable for being inserted into interspaces between teeth and having said triangular cross-section gradually decreasing in cross-section from said bent portion to an end thereof for outlet of paste; and wherein two opposed broad faces of said cap define an outlet aperture means for the paste.

4. A device according to claim 3, wherein said cap is formed with transverse grooves, in the bottom of which said outlet aperture means terminate.

* * * * *